(12) United States Patent
Meijer et al.

(10) Patent No.: US 6,787,151 B2
(45) Date of Patent: Sep. 7, 2004

(54) COMPOSITION FOR LOWERING BLOOD CHOLESTEROL

(75) Inventors: Geert Willem Meijer, Mahwah, NJ (US); William Conrad Franke, Cranbury, NJ (US); Podutoori Ravinder Reddy, Bethesda, MD (US)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 30 days.

(21) Appl. No.: 09/928,027

(22) Filed: Aug. 10, 2001

(65) Prior Publication Data

US 2003/0108591 A1 Jun. 12, 2003

(51) Int. Cl.[7] .............................................. A61K 47/00
(52) U.S. Cl. ..................................................... 424/439
(58) Field of Search ................................ 424/439, 757; 514/2, 170; 426/72

(56) References Cited

U.S. PATENT DOCUMENTS

| | | | |
|---|---|---|---|
| 4,157,984 A | 6/1979 | Zilliken | |
| 4,390,559 A | 6/1983 | Zilliken | |
| 5,424,331 A | 6/1995 | Shlyankevich | |
| 5,506,211 A | 4/1996 | Barnes et al. | |
| 5,654,011 A | 8/1997 | Jackson et al. | |
| 5,776,906 A | 7/1998 | Sekiya | |
| 5,807,586 A | 9/1998 | Jackson et al. | |
| 5,830,807 A | 11/1998 | Matsunaga et al. | |
| 5,830,887 A | 11/1998 | Kelly | |
| 5,855,892 A | 1/1999 | Potter et al. | |
| 5,858,449 A | 1/1999 | Crank et al. | |
| 5,892,068 A | 4/1999 | Higgins | |
| 5,958,913 A | 9/1999 | Niettenen et al. | |
| 6,031,118 A | 2/2000 | Van Amerongen | |
| 6,106,886 A | 8/2000 | Van Amerongen | |
| 6,184,397 B1 | 2/2001 | Roden et al. | |
| 6,231,915 B1 | 5/2001 | Van Amerongen | |
| 6,241,996 B1 * | 6/2001 | Hahn ......................... | 424/439 |
| 2001/0024666 A1 * | 9/2001 | Waggle et al. .............. | 424/757 |
| 2002/0155194 A1 * | 10/2002 | Mehansho et al. ........... | 426/72 |

FOREIGN PATENT DOCUMENTS

| | | |
|---|---|---|
| EP | 1 046 396 | 10/2000 |
| WO | 96/10341 | 4/1996 |
| WO | 98/03084 | 1/1998 |
| WO | 98/08503 | 3/1998 |
| WO | 98/21946 | 5/1998 |
| WO | 00/03684 | 1/2000 |
| WO | 00/30663 | 6/2000 |
| WO | 00/30665 | 6/2000 |
| WO | 00/45650 | 8/2000 |

* cited by examiner

*Primary Examiner*—Karen Cochrane Carlson
*Assistant Examiner*—Sheridan Snedden
(74) *Attorney, Agent, or Firm*—Gerard J. McGowan, Jr.

(57) ABSTRACT

Ingestable products for lowering blood total cholesterol, including isoflavone, vegetable protein such as soy protein and phytosterol. The combination of phytosterol with soy protein (which includes isoflavone) is superior to the individual components alone in improving plasma lipid profiles. Preferably the products are food products. The invention is also a method for lowering plasma cholesterol in animals, preferably humans, by feeding compositions having plasma cholesterol-lowering, synergistically effective amounts of isoflavone, soy protein and phytosterol.

32 Claims, No Drawings

COMPOSITION FOR LOWERING BLOOD CHOLESTEROL

BACKGROUND OF THE INVENTION

The following abbreviations are used in the course of the present application:

| | |
|---|---|
| LDL | Low density lipoproteins |
| TC | Total cholesterol (including free cholesterol and cholesteryl ester) |
| TG | Triglycerides |
| VLDL | Very low density lipoproteins |
| CHD | Coronary Heart Disease |
| MUFA | Mono-unsaturated fatty acid moieties |
| PUFA | Poly-unsaturated fatty acid moieties |

Despite considerable research efforts over the years, coronary heart disease (CHD) remains a formidable threat to the health of people in many countries throughout the world. Among factors considered to be of predictive value concerning the risk of CHD, an important traditional one has been blood total cholesterol (TC) levels, while in recent years the relative amounts of HDL cholesterol and LDL cholesterol have been linked to risk of CHD. High ratios of HDL to LDL are now generally considered as an indicator of salutary cardiac status.

Phytosterols, i.e., plant sterols, are well documented to have a hypocholesterolemic effect. Phytosterols inhibit intestinal cholesterol absorption, thereby lowering blood total and low-density lipoprotein (LDL) cholesterol concentrations. In human studies, phytosterols have been shown to reduce blood cholesterol concentration by an average of 10%. Moghadasian M H, Frohlich J J, "Effects of dietary phytosterols on cholesterol metabolism and atherosclerosis: clinical and experimental evidence." Am J Med 1999;107:588–594.

Soy protein is among a number of other food ingredients which have been well documented to have a hypocholesterolemic effect. Dietary intake of soy protein has been associated with reduced blood cholesterol concentrations and a lower incidence of coronary heart disease based on a number of the reports obtained from animal, (Potter S M. "Overview of proposed mechanisms for the hypocholesterolemic effect of soy." J Nutr 1995;125:606S–611S), human (Cassidy A, Bingham S, Setchell K D. "Biological effects of a diet of soy protein rich in isoflavones on the menstrual cycle of premenopausal women," Am J Clin Nutr 1994;60:333–340; Teixeira S R, Potter S M, Weigel R, Hannum S, Erdman J W J, Hasler C M. "Effects of feeding 4 levels of soy protein for 3 and 6 wk on blood lipids and apolipoproteins in moderately hypercholesterolemic men," Am J Clin Nutr 2000;71:1077–1084,) and epidemiological (Hollman P C, Katan M B. "Dietary flavonoids: intake, health effects and bioavailability," Food Chem Toxicol 1999;37:937–942) studies.

The mechanisms by which soy protein exerts its hypocholesterolemic effect may be different from that of phytosterols. It is generally assumed that the cholesterol lowering effects of soy protein are mediated through an increased plasma cholesterol clearance and/or an increased bile acid formation and excretion (Cassidy A, Bingham S, Setchell K D, "Biological effects of a diet of soy protein rich in isoflavones on the menstrual cycle of premenopausal women," Am J Clin Nutr 1994;60:333–340; Lichtenstein A H. "Soy protein, isoflavones and cardiovascular disease risk," J Nutr 1998;128:1589–1592; Baum J A, Teng H, Erdman J W J, et al. "Long-term intake of soy protein improves blood lipid profiles and increases mononuclear cell low-density-lipoprotein receptor messenger RNA in hypercholesterolemic, postmenopausal women," Am J Clin Nutr 1998;68:545–551).

Although the cholesterol lowering effect of soy protein is well documented, the component(s) responsible for this effect in soy protein are still not identified. Soy protein is a rich source of isoflavones. While several studies appear to have demonstrated that the isoflavones in the soy protein may be the cause of the cholesterol lowering effect, (Merz-Demlow B E, Duncan A M, Wangen K E, et al. "Soy isoflavones improve plasma lipids in normocholesterolemic, premenopausal women," Am J Clin Nutr 2000;71:1462–1469; Anthony M S, Clarkson T B, Williams J K, "Effects of soy isoflavones on atherosclerosis: potential mechanisms, Am J Clin Nutr 1998;68:1390S–1393S; Ni W, Yoshida S, Tsuda Y, Nagao K, Sato M, Imaizumi K., "Ethanol-extracted soy protein isolate results in elevation of serum cholesterol in exogenously hypercholesterolemic rats," Lipids 1999;34:713–716; Crouse J R, Morgan T, Terry J G, Ellis J, Vitolins M, Burke G L, "A randomized trial comparing the effect of casein with that of soy protein containing varying amounts of isoflavones on plasma concentrations of lipids and lipoproteins," Arch Intern Med 1999;159:2070–2076), other studies appear to have shown that the soy protein itself (including soy amino-acids or peptides) or the protein-associated substances other than isoflavones exhibited a cholesterol lowering activity (Greaves K A, Wilson M D, Rudel L L, Williams J K, Wagner J D. "Consumption of soy protein reduces cholesterol absorption compared to casein protein alone or supplemented with an isoflavone extract or conjugated equine estrogen in ovariectomized cynomolgus monkeys," J Nutr 2000;130:820–826).

A hypotriglyceridemic effect of soy protein in human subjects was noted in a meta-analysis by Anderson J W, Johnstone B M, Cook-Newell M E in "Meta-analysis of the effects of soy protein intake on serum lipids," N.Engl.J Med 1995;333:276–282.

Other ingestable materials which have been suggested in scientific literature or the press as causing improvement in cholesterol status or potential cholesterol improvement effects include: statins, niacin, inositol hexaniacinate, Vitamin E, tocotrienols, vitamin C, pantethine, quercetin, chromium, calcium, magnesium, L-carnitine, soy, chondroitin sulfate, lecithin, chitosan, royal jelly and copper. Despite the many agents which have been mentioned thus far in the scientific and popular literature as having potential cholesterol improving benefits in animals and humans, there is still a serious need for many individuals to improve further their cholesterol status, preferably without resorting to pharmaceuticals.

The problem of elevated cholesterol levels has received considerable attention in the patent literature, as well.

Potter et al., U.S. Pat. No. 5,855,892 discloses that daidzein and its metabolites, o-desmethylangolensin and dihydrodaidzein are useful for altering the concentration of cholesterol constituents in the blood of a human by increasing the concentration of high density lipoprotein cholesterol and decreasing the concentration of low density lipoprotein cholesterol. Potter et al. also report that vegetable protein materials, particularly soy protein materials, are known to reduce total cholesterol and LDL-cholesterol levels in the blood of animals.

Phytoestrogens in the soy protein are said to be recognized as a potentially significant factor in the hypocholesteremic effects of soy protein, and estrogen itself is said to be determined to be a significant cardio protective factor. In their background discussion, Potter et al. report that recent studies have determined that isoflavones lower blood concentrations of total cholesterol and LDL cholesterol in animals and thereby inhibit or slow the development of atherosclerosis, but that the effect of these isoflavones on blood cholesterol level in humans has been less clear.

The Potter et al. invention is directed to a method of altering the concentration of the cholesterol constituents in the blood of a human to reduce the risk of atheroschlerosis and vascular disease by administering a material containing daidzein to a human in an amount effective to increase the concentration of HDL cholesterol and to decrease the concentration of LDL cholesterol in the blood of a human. In one embodiment, daidzein is administered in a human in a soy protein material dietary supplement. Dietary supplements incorporating daidzein can be prepared by adding daidzein to a food which is said to include almost all foods, such as beverages, including nutritional beverages, frozen desserts such as ice cream, ice milk, low fat frozen desserts and non-dairy frozen desserts, soups, salad dressings and dips and spreads such as mayonnaise and chip dips. Acceptable and effective daily doses are said to be from about 10 to about 1,000 milligrams per day, more typically from about 30 to about 500 milligrams per day and most preferably from about 50 to about 300 milligrams per day. A soy yogurt is formulated having in a 170 gram serving about 8 grams of soy protein having about 8–24 milligrams of daidzein therein.

WO 00/45650 (International filing date Feb. 7, 2000, publication date "Calcium Supplemented Food Products and Novel Calcium-Containing Ingredient" and relates to foods and drinks and particularly to an emulsified fat spread which is supplemented with calcium. It is said that the spreads and other foods and drinks can be supplemented with vitamins, such as vitamins A and D, and with any other additives known to be beneficial to human health. Examples given include plant sterols or their esters to provide the additional benefit of cholesterol lowering, other vitamins and minerals, carotenoids (e.g., lycopenes), alpha tocopherol, antioxidants (e.g., ascorbic acid, flavonoids and isoflavones), lutein and other phytochemicals. In example 17, soy isoflavones are added to a spread. In claim 29, a food product or beverage is claimed having a food additive selected from the group consisting of vitamins, minerals, plant sterols, lycopenes, carotenoids, flavonoids, isoflavones, antioxidants, lutein and mixtures thereof. Proteins present in milk-derived solids are said to interact with nucleation sites or small crystals or particles of calcium salts to alter the normal course of crystallization or precipitation. It is said that proteins from other sources, eg., soya proteins or other plant-derived proteins and other food additives with one or more of the same functional groups, ie, carboxyl, hydroxyl, amino, amido, thiol or phenol groups when added to an aqueous solution prior to combining a calcium source with a source of anions should exert a similar influence on the organoleptic properties of the calcium composites when incorporated into emulsified fat spreads or other food and drink formulations.

WO 00/64276, published Nov. 2, 2000, is directed to spreads supplemented with isoflavones. It is said that phytosterols may also be added at up to 20 wt. %, especially up to 10 wt. % and that soy proteins may be added at between 0.4 wt. % and 2 or 3 wt. %. Priority from a US application is claimed.

WO 00/30665 published Jun. 2, 2000, discloses a composition comprising soy protein, a phytoestrogen compound and dietary fibers said to be useful to lower serum cholesterol and LDL cholesterol and serum triglycerides, and for increasing the HDL/LDL ratio. In claim 38 a composition further including a sterol is recited whereas in claim 39 a further compound which may be a stanol ester or a phytosterol is included. Various food products such as spreadable products, nutritional bars, liquids for drinking, etc. are mentioned.

WO 00/30663, published Jun. 2, 2000, discloses a composition comprising soy protein, a phytoestrogen compound and dietary fibers said to be useful to treat type 2 diabetes and cardiovascular diseases in a diabetic subject. The compositions can be used as a medicament and/or in the manufacture of a medicament. The composition can further include a sterol which may be a stanol ester or a phytosterol such as sitosterol. Various food products such as spreadable products, nutritional bars, liquids for drinking, etc. are mentioned. Alternatively, the invention provides a composition wherein no dietary fibres are present. Use in amounts effective in serum cholesterol levels and/or lowering LDL-cholesterol levels is mentioned.

WO 93/23069 discloses compositions enriched with phytoestrogens, or analogs, selected from genistein, daidzein, formononetin, and Biochanin A as a food additive, tablet or capsule for promoting health in cases of cancer, premenstrual syndrome or hypercholesterolaemia. Soy is among the many possible sources of phytoestrogens mentioned.

Setchell, et al. "Mammalian Lignans and Phytoestrogens Recent Studies on their Formation, Metabolism and Biological Role in Health and Disease," "Role of the Gut Flora in Toxicity and Cancer," pp. 315–345 (1988), mentions interest in studies on the role of intestinal bacteria metabolism on hormones, bile acids and sterols.

Crank et al., U.S. Pat. No. 5,858,449 is directed to isoflavone-enriched soy protein products and methods for their manufacture. The product may be an ingredient in dairy or meat based food products such as infant formula, nutritional beverage, milk replacer, bologna, imitation processed cheese spread, water-injected ham, yogurt and frozen dessert. Crank et al., also discloses a method of making an isoflavone enriched soy product.

Example 5 discloses a soy based imitation processed cheese spread. Example 8 discloses a soy-based frozen dessert and a yogurt. The yogurt includes whey, vegetable oil, sugar, emulsifiers, salts, vitamins and minerals. The soybean products include daidzein, genistein, and glycitein.

Kelly, U.S. Pat. No. 5,830,807 is directed to compositions enriched with natural phytoestrogens or analogs thereof selected from genistein, daidzein, formononetin and biochanin A. It is said that they may be used as food additives, tablets or capsules for promoting health in cases of cancer, premenstrual syndrome, menopause or hyercholesterolaemia. Formulations may include drinks, solutions, syrups, etc.

WO 98/08503 discloses administration of an isoflavone-type compound used for various conditions including menopausal syndrome such as hot flashes, anxiety and depression, moods, swings, night sweats, headaches urinary incontinence, osteoporosis, premenstrual syndrome, fluid retention, cyclic mastalgia dysmenorrhea, Raynaud's syndrome, Raynaud's phenomenon and Buerger's diseases, coronary artery spasms, migraine headaches, hypertension, benign prostatic hypertrophy, cancers of the breast, uterus, ovary, colon, endometrium, testicle, prostate, or large bowel, cyclical mastalgia, aeterosclerosis, Alzheimer's disease, male impotency, inflammatory bowel syndrome, ulcerative colitis, Crohn's disease, inflammatory effects such as rheumatoid diseases including rheumatoid arthritis acne, baldness, including male pattern baldness, psoriasis and diseases associated with oxidant stress including cancer, myocardial infarction, stroke, arthritis, sunlight induced skin damage or cataracts, and oxidant related disorders, inflammatory diseases, menopausal syndrome, anxiety, depression, mood swings, acne, estrogenic effects, androgenic effects, vasodilatory and spasmodic effects. It can be used with Vitamin E. Use as additives in foods and drinks such as health bars or desserts is mentioned.

The term "food stuffs," is said to be used in as wide as possible sense. It includes liquid formulations such as drinks, including dairy products, and other foods. Health drinks are mentioned.

Gorbach et al, U.S. Pat. No. 5,498,631 is directed to a method for treating symptoms of menopause, premenstrual syndrome or a condition resulting from reduced levels of indigenous estrogen by administering to the women an effective amount of an isoflavoid. Isoflavonoids which may be administered include genistein, daidzein, biochanin A, formononetin, o-desmethylangolensin and equol. The invention is said to feature a therapeutic dietary product for preventing or treating symptoms resulting from reduced or altered levels of indigenous estrogen. The dietary products preferably include a soy extract containing enriched isoflavonoids provided in a palatable food carrier, (e.g. a confectionery bar, biscuit, cereal or beverage).

WO 00/03684 discloses soy formulations comprising 3–23 milligrams of at least one isoflavone per gram, and which may also include 0.4 to 1.2 grams of protein per gram. The compositions may additionally include a medicinal composition such as drugs or prescription drugs utilized in estrogen replacement therapy, hormone replacement therapy, cholesterol lowering therapy, bone strengthening therapy, endometrial therapy, cancer therapy, Alzheimer's therapy, ulcer therapy, prostrate therapy, skin therapy, renal therapy, blood therapy, lymphatic therapy, lung therapy, nervous system therapy, diabetes therapy, eye therapy and the like.

Jackson et al. U.S. Pat. No. 5,807,586 discloses a method of supplementing the dietary needs of women with many ingredients, including phytoestrogens.

Sekiya et al., U.S. Pat. No. 5,776,906 is directed to a method for promoting fat degradation comprising administrating to a human a composition containing an effective amount of an isoflavone, thereby promoting fat degradation in the fat cell. Soybean is mentioned as a potential source and daidzein, daidzein, genistein, genistin and derivatives thereof are mentioned. When the compositions intended to be a food it contains five to 1,000 milligrams-milliliter (g) of isoflavone.

Barnes et al., U.S. Pat. No. 5,506,211 discloses that the isoflavone genistein inhibits the acid secretion of osteoclasts and reduces bone resorption. The claims mention use of a genistein/glucoside conjugate. To reduce osteoclastic acid secretion one would generally contact one or more osteoclasts with a composition that comprises a biologically effective amount of genistein. Foodstuffs such as soy which contain genistein or concentrated forms thereof may be ingested to provide an animal with an effective amount of genistein. Various soy products such as soy protein may be used.

In human treatments, suitable methods include administering from 2 to 50 milligrams to 20 to 50 milligrams of genistein in the form of a food product. This may be achieved by ingesting between about 2 to 50 milligrams or about 20 to 50 milligrams of isolated soy protein per day per person. Barnes et al. acknowledge that genistein is known to be a tyrosine kinase inhibitor and has been proposed for use in treating several diseases and disorders, for example cardiovascular disease, atherosclerosis and certain cancers.

Jackson et al., U.S. Pat. No. 5,654,011 (Energetics) filed Jul. 30, 1996 is directed to a dietary supplement for supplementing the nutritional needs of pre-perimenopausal women.

Kelly, U.S. Pat. No. 5,830,887 is directed to compositions enriched with natural phytoestrogens selected from genistein, daidzein, formononetin and biochanin A. These may be used as food additives, tablets or capsules for promoting health in cases of cancer, premenstrual syndrome, menopause, or hyercholesterolaemia. In Example 4, soy hypocotyl was consumed as a powder added to the diet.

Liu et al., "A comparison of pharmacodynamics between daidzein and a solid dispersion of daizein", Shenyang Yaoxueyuan Xuebao, 1990, Vol. 7, No. 2, 123–5, pp 131 discloses that daidzein is used in clinical treatment of hypertension and coronary atherosclerotic heart disease, but is absorbed so slowly that is begins to show the effects only in a week's time. A solid dispersion of daidzein is disclosed, and results are said to show that at equal dosage levels the solids dispersion produced more significant results on arrhythmia induced by $BaCl_2$ in anesthetized rats.

Zilliken, U.S. Pat. No. 4,157,984 is directed to antioxidant compositions useful as stabilizers for food compositions including edible fats and oils. The compositions are prepared from a natural source, tempeh, a fermented soybean product. An ergostadientriol which possesses antioxidative properties and which in combination with mixtures of isoflavones provides compositions having exceptional antioxidative properties is disclosed. This can be used alone or in mixtures with isoflavones or other compounds.

Shlyankevich, U.S. Pat. No. 5,424,331 (Biovirus Research) is directed to a composition for treatment or prevention of osteoporosis which includes one or more phytoestrogen compounds, calcium contained in a biologically acceptable calcium salt, magnesium contained in a biologically acceptable magnesium salt, zinc contained in a biologically acceptable zinc salt, beta carotene, vitamin D and vitamin E. The compositions may be administered either as a dietary supplement or as a pharmaceutical.

WO 9610341 (Schouten Industries) discloses substantially pure hypocotyls of Glycine max which may be used in food and other products. They may be used as raw materials for isolation of isoflavones such as daidzin, genistin and glycitin. They may be incorporated in drinks, dairy products, bakery products, health teas and other products. In Example 2, a tomato juice cocktail is disclosed including tomato concentrate, green tea natural, beta carotene, natural vitamin E and Glycine max hypocotyl. The product contained 10 mg genistein/daidzein as glucosides per can of 163 ml.

Zilliken U.S. Pat. No. 4,390,559 is directed to isoflavones useful as antioxidants and useful in antioxidant compositions including edible fats and oils.

Schouten Industries, USA sells a soybean isolate product called SoyLife® comprising 40.5% protein, 11.2% fatty acid, 3.0% isoflavones, and 4.1% saponins. They suggest incorporating 1% to 5% of the SoyLife® product in any foods, including dietary drinks.

SUMMARY OF THE INVENTION

The present invention is directed to the discovery that three heretofore known classes of cholesterol lowering agents, soy protein, isoflavones (present within soy protein in nature), and phytosterols, when used in combination produce a greater cholesterol improvement effect than would be expected from data obtained from the use of fewer than all three together. It is contemplated that other vegetable proteins may be used in place of soy protein.

It has been discovered that a combined intervention with phytosterols and soy protein (including isoflavones) gives a clear synergistic hypocholesterolemic effect. Indeed, although the number of subjects tested thus far is insufficient for a rigorous confirmation of statistical significance, the combination has been found to have a greater-than-additive effect. Particularly in view of a previous (hamster) study conducted in a similar experimental conditions which demonstrated that by increasing dietary phytosterols supplementation from 0.24 to 0.48% (w/w) no extra hypocholestemic effect were achieved, the synergistic, indeed, greater than additive, cholesterol lowering effect of the combination of phytosterols and soy protein is surprising and can be expected to provide a useful tool in treating hypercholesterolemia in animals, particularly in humans.

While not wishing to be bound by theory, the action of the combined ingredients according to the invention might be related to different reported bioactivities between phytosterols and soy protein. It has been demonstrated that phytosterols inhibit intestinal cholesterol absorption, while soy proteins increase LDL receptor activity. Other studies have shown that soy protein increased hepatic cholesterol 7 alpha-hydroxylase activity, which enhances bile acid production. Therefore, from the additive action it can be presupposed that soy protein lowers blood cholesterol via increased removal of LDL from blood by increasing LDL-receptor activity and hepatic bile acid and cholesterol secretion into the intestines. This action is enhanced by phytosterols which inhibit cholesterol (re-)absorption from the intestines.

In addition to the cholesterol lowering effect, the combination significantly lowers blood triglyceride concentrations. This finding is in accordance with the hypotriglyceridemic effect of soy protein in human subjects as noted in the meta-analysis (Anderson et al.) mentioned above. Blood VLDL is the major carrier of blood TG in a fasting state. This suggests that the TG-suppressing effect of soy protein might be due to a suppressed VLDL production or metabolism. Since an increase of blood TG concentration has been assumed to be an independent risk factor for the development of cardiovascular disease, the combination of phytosterol with soy protein might have extra benefit in reducing the risk of cardiovascular disease.

While soy protein is a significant component of the inventive compositions, it is not believed that dietary fiber, e.g., soy fiber, contributes importantly. Therefore, the present compositions preferably include little or no soy or other dietary fiber. In particular, the compositions preferably include less than 4 wt %, especially less than 3 wt. % and more preferred less than 1 wt % or less of soy or other dietary fiber.

The compositions of the invention including the above described combination of cholesterol-lowering ingredients may take many forms, such as capsules, pills and gellcaps, but are especially foods such as, spreads, frozen desserts, beverages and nutritional bars.

Examples of preferred food products according to the invention are margarines or other spreads of oil based products, bakery products, dairy products, e.g. yogurt, cheese and milk-based drinks, beverages, e.g., soft drinks, fruit juices and tea and coffee based drinks, sauces, dressings and mayonnaise and confectionery products, e.g., frozen confectionery products such as water-ice or ice-cream. Especially preferred is the use in food products selected from the group of margarines and other spreads, tea based beverages, dressing and frozen confectionery products.

The spread is advantageously prepared by combining a fat phase with an aqueous phase, after which the mixture is processed into an emulsion and the isoflavones, soy protein and phytosterols and other additives are added.

For some foods, it will be possible to include the effective amounts of the ingredients in a single serving, whereas for others, it may be necessary to use multiple servings and/or combine servings of different foods. Keeping in mind, then, that it will not be possible with all foods to achieve the desired levels in a single serving, levels of the ingredients preferably used in accordance with the invention per serving are from 1 to 25 g soy or other vegetable protein (exclusive of any included isoflavone or phytosterol), from 5 to 150 mg isoflavone and from 0.2 to 3 g phytosterol. Especially preferred levels are from 1 to 8, or better from 3 to 7 g soy protein (exclusive of any included isoflavone or phytosterol), from 10 to 100 mg isoflavone and from 0.4 to 2.5 g phytosterol. Most preferred levels are from 5 to 6.5 g soy protein (exclusive of any included isoflavone or phytosterol), from 15 to 50 mg isoflavone and from 0.6 to 1.7 g phytosterol.

Depending on the intended consumer of the product, products of the invention may be supplemented with calcium, or, if desired, calcium supplementation can be omitted and/or calcium levels limited to provide a calcium-free or essentially calcium-free product. For instance the product may have less than about 1.5 wt. %, especially less than 0.5 wt. % or 0.1 wt. % total calcium salts (as salt) in the product. Most preferably, the products may have less than 0.5 wt %, especially less than 0.3 wt %, more preferably less than 0.1 wt % calcium based measured as calcium. Alternatively where calcium supplementation/higher levels or calcium are desired in the product, preferred calcium levels are given below. Where calcium is included, it is not generally necessary in accordance with the present invention to combine the individual constituents of the same calcium salts and precipitated in an aqueous solution of milk derived solids. Although the coprecipitation can generally be avoided, it may be useful in some situations. Where used, the calcium may be a soluble or an insoluble salt.

For a more complete understanding of the above and other features and advantages of the invention, reference should be made to the following detailed description of preferred embodiments and to the accompanying drawings.

DETAILED DESCRIPTION OF THE INVENTION

Preferred sources of isoflavones include soy, clover, including red clover and subterranean clover, grains, chickpeas, ground nuts, lentils and beans, at levels of between 40 and 500 mg/100 g dry weight. Isoflavones are found in plants primarily bound to sugars such as glucose, as glycosides. Smaller amounts are found in plants in the aglucone form. The present invention encompasses addition of isoflavones in either bound and/or the free forms.

Soy may be used, for example, in the form of soybean flour; or the hull and/or hypocotyl may be used.

Processes for isolating phytoestrogens and phytoestrogen moiety-containing compounds and complexes from plants are well known. These include the process of Fluery et al. U.S. Pat. No. 5,141,746, the disclosure of which is incorporated by reference, Gugger et al. U.S. Pat. No. 5,702,752 and Shen et al. U.S. Pat. No. 5,637,562. Phytoestrogens are also available in the form of soy isoflavone concentrate obtained from soy flour and sold under the Soylife® trade name by Schouten USA, Inc. of Minneapolis, Minn. An additional source of phytoestrogens is Novasoy available from ADM.

Preferred levels of the phytoestrogens are at least 0.01 wt. % on the total weight of the product, which is preferably a food product, especially at least 0.05 wt. %.

By "phytosterols" herein is meant plant sterols, esters of plant sterols, plant stanols or stanol esters and stanols and stanol esters derivable from plant sterols. Examples include sitosterol, sitostanol, their fatty acid esters, and the like. These may be included from 1 to about 20 wt. %, especially up to about 10 wt. % of the food product based on the sterol moiety.

More specifically, examples include alpha sitosterol, beta sitosterol, stigmasterol, ergosterol, campesterol, alpha sitostanol, beta sitostanol, campestanol and brassiciasterol. Although the foregoing are some of the more important phytosterols, at least 44 phytosterols have been identified and it will be apparent to one of ordinary skill that many of these will be appropriate for the present invention. Oryzanol may also be used. Phytosterols are identified in bean (1993) phytosterols in "Advance in Lipid Research", pages 193–218, Paoletti, and Kiritchevsky, (Eds) Academic press, NY, the disclosure of which is incorporated herein by reference. The disclosure of "Effect of Plant Sterols on Lipids and Atherosclerosis", Pollack, O. J., Pharmac, Ther., 31, 177–208 (1985) mentioned above is also incorporated by reference herein.

Among the more important sources are rice bran, corn bran, corn germ, wheat germ oil, corn oil, safflower oil, oat oil, olive oil, cotton seed oil, soybean oil, e.g., soybean oil distillates, peanut oil, black tea, orange juice, valencia, green tea, Colocsia, kale, broccoli, sesame seeds, shea oils, grapeseed oil, rapeseed oil, linseed oil, canola oil, tall oil from wood pulp and other resinous oil from wood pulp.

Soy protein can be obtained from numerous sources, including the Soylife® product mentioned above and Supro® from Dupont.

Spreads

A beneficial form for ingestion of isoflavones, soy protein and phytosterols is in the form of a water-in-oil spread, particularly a bread spread. It can be expected that the reported beneficial health effects of isoflavones, phytosterols and soy protein may be enjoyed by the consumer by consuming the spread without the need for pharmaceutical-type products, e.g., pills, capsules, etc. although these are within the invention as well.

In another preferred embodiment, the spread is an emulsion comprising added isoflavones, soy protein, phytosterols and at least 0.25 wt. % of a calcium salt, especially at least 0.5 wt. % of a calcium salt. The spread is preferably a water-in-oil emulsion. The spread is an excellent vehicle to provide women with the phytoestrogens and calcium both of which have enjoyed favorable reports concerning health effects.

In another preferred embodiment of the invention, the spread is an emulsion comprising isoflavones, soy protein, phytosterols and one or more, preferably at least two, of the following vitamins: A, D, E, B6 and B12. Preferably the spread also includes elevated levels of calcium and/or magnesium. Preferably this spread is also a water-in-oil emulsion.

Preferably a spread is provided with isoflavones, soy protein, phytosterols and a level and type of triglycerides such that at least 5 wt. % polyunsaturated fatty acid moieties are present (based on the total weight of the spread) to provide consumers with access to these substances in a beneficial food form. More preferably, the level and type of triglycerides is selected so that the spreads include at least 7 wt. %, especially up to a level of 20 wt. % polyunsaturated fatty acid moieties.

Isoflavones which may be used include genistein, daidzein, genistin, daidzin, equol, glycitein and glycitin.

Spreads according to the invention generally contain from less than 80% by weight of edible triglyceride materials. Suitable edible triglyceride materials are for example disclosed in Bailey's Industrial Oil and Fat Products (1979). In higher fat spreads, the level of triglyceride material will generally be more than 60% and less than 80%, preferably from 70 to 79% by weight. In spreads of reduced fat content the level of triglycerides will generally be from 30–60%, more generally from 35 to 45% by weight. In very low fat spreads the level of triglycerides will generally be from 0 to 40%, for example, 30%, 25%, 20% or even 10% or about 0%.

Optional ingredients in the fat-continuous phase which is combined with the aqueous composition include emulsifiers, salt (particularly sodium chloride), preservatives, flavors, protein, vitamins, especially fat soluble vitamins such as vitamin A, antioxidants, antimicrobials, and preservatives, including citric and other acids. The emulsifiers can include mono- and diglycerides, polyglycerol esters, lecithin and polyoxyethylene sorbitan monoesters such as TWEEN 60 and TWEEN 80. One advantageous emulsifier is a polyglycerol polyricinoleate sold under the name Admul Wol available from Quest International, Naarden, the Netherlands.

Emulsifiers may be included at from 0.05 to 2% by weight, typically not more than 1% by weight.

It is preferred that the fat used is triglyceride fat derived from vegetable sources including soybean, canola, corn, sunflower, palm, Palm kernal, rapeseed, coconut, safflower, cottonseed, peanut and olive oils. Other digestible fat sources which may be used are fish oil, milk fat, skim milk fat, butterfat, lard and tallow. The oil will be hardened by hydrogenation if that is necessary to achieve the desired melting characteristics. Also, fractionation and interesterification may be used to obtain fats of the desire melting range. Especially preferred are fats having relatively large proportions of polyunsaturated fatty acid moieties, such as canola and soybean oils. The fat compositions mentioned in Netherlands patent documents No. NL 143115, NL 178559, NL 155436, NL 149687, NL 155177, and European patent documents EP 41303, EP 209176, EP 249282, and EP 470658, the disclosures of which are incorporated by reference, are highly suitable. If a fat blend is used it is most preferred that it comprises at least 30%, more preferably at least 45% of polyunsaturated fatty acid moieties, based on the total weight amount of the fat in the fat based food product to promote cholesterol lowering.

The fat can be a single fat or a blend. The use of a fat composition comprising a considerable amount of PUFA (polyunsaturated fatty acid) rich triglycerides is in particular considered highly beneficial.

Non-digestible fats may also be used as the fat source. Among the non-digestible fats are included polyol polyesters of $C_8$ to $C_{22}$ fatty acids such as sucrose polyester, sucrose polyethers, silicone oils/siloxanes, polycarboxylic acid esters, branched chain fatty acid triglycerides, neopentyl alcohol esters, dicarboxylic acid esters, jojoba oil and triglycerol ethers. Non-digestible fats may be used as from 0 to 100% of the fat, especially from 10 to 90%, and most especially from 25 to 75%.

Non-lipid fat replacers may also be used, to provide body to the product. These include protein-based fat replacers such as those described in Singer et al., U.S. Pat. No. 4,961,953 and cellulosic bulking agents such as microcrystalline cellulose and carboxymethyl cellulose.

Coloring agents, such as beta carotene, paprika, turmeric, annatto and yellow #5 and 6 and combinations thereof may be employed. The yellow color may desirably be used in combination with an opacifier like $TiO_2$. It has been found that providing an appropriate color may be important since phytoestrogen sources such as soy flour impart a brownish color.

The soy protein which may be present in the compositions of the invention, may be present with the phytoestrogens which are added to the spread, as in soy flour.

Other vegetable proteins, such as peanut protein, cottonseed protein and the like may be used together with, or instead of, soy. In addition to soy proteins or other vegetable proteins, other proteins, if desired, can conveniently be included in the form of milk protein from whole, skim or other low fat milk and may comprise whey proteins (with or without lactose), acid casein and caseinates.

In addition to sodium chloride, flavor enhancers which may be employed include lactones, lipolyzed butter oils and started distillates, diacetyl, 2-octanone, butyric acid, hexanoic acid, and other fatty acids, esters of butyric acid, hexanoic acid, and other fatty acids, esters of butyric acid, delta-hydroxy acids and their glycerol esters and mixtures thereof.

Preservatives, such as benzoic acid, sorbic acid, phosphoric acid, lactic acid, acetic acid, hydrochloric acid and the soluble salts thereof may be used.

Antioxidants may include normal propyl gallagte, the tocopherols, including Vitamin E, butylated hydroxyanisole (BHA), butylated hydroxytoluene (BHT), nordihydorguaiaretic acid (NDGA), tertiary-butylhydroquinon (TBQH) and citric acid. Metal chelators or sequestrants such as sodium calcium salts of ethylenediamine tetra acetic acid (EDTA) may also be used.

Where the product takes the form of a water/oil emulsion, it will be appreciated that normally more hydrophobic additives will be added to the fat phase whereas more hydrophilic additives will normally be added to the aqueous phase.

The aqueous phase comprises water and, optionally other ingredients. A preferred ingredient is one or more gelling agents such as gelatin. Where the spread is a low fat spread, it is advantageous that the aqueous composition is gelled, which in some respects compensates for the lower amounts of fat in the product. It may be advantageous for the aqueous composition to be pre-gelled, i.e., gelled prior to combining the aqueous composition with the fat-continuous emulsion. Other suitable gelling agents include waxy maize starch such as Ultra-Tex 2, available from the National Starch and Chemical co., Bridgewater, N.J. or a rice starch such as Remyrise AC. A particularly effective combination of gelling agents has proved to be gelatin and waxy maize or rice starch. Other gelling agents include carrageenan, and a gelling hydrolyzed starch derivatives such as gelling maltodextrin, for example, Paselli maltodextrin SA2®.

The amount of gelling agent may lie between 0 and 30%, mostly between 0.1 and 25% based on the weight of the aqueous phase of the spread. If hydrolyzed starches are present, their level may be from 2–20%; other gelling agents may be used at levels of up to 10%, mostly 1–7%, most preferred 2–5%, all of these percentages being based on the weight of the aqueous phase.

Hydrocolloids which are thickening rather than gelling agents may also be used. Hydrocolloids are described in Zeitschrift fur Lebenmittletechnologie und Verfahrenstechnk 32 (1981) 6, pp. 253–256. Hydrocolloids in addition to those mentioned above include polysaccharides such as native and modified starches, cellulose derivatives, pectins, galleon, xanthan gum, agar, Danish agar, furcelleran, gum arabic, guar gum, locust bean gum, algin, and alginates. Hydrocolloids will generally be used at levels of from 0.2 to 6%, based on total products. It will be appreciated that the gelling and thickening agents may be used in various combinations.

Additional ingredients which may be present in the aqueous phase include salt (particularly sodium chloride), preservatives, such as potassium sorbate, lactic and other acid, proteins, coloring agents, flavors, antimicrobials, antioxidants and vitamins, particularly water-soluble vitamins such as the B vitamins.

Addition of strong flavoring such as fruit purees, fruit flavors including vanilla and savory ingredients such as oregano and/or garlic, as well as spices and sugar can be important in masking off flour of phytoestrogen sources such as soy.

Proteins, water-soluble coloring agents, flavors, preservatives and antimicrobials and antioxidants useful in the aqueous composition are the same as those discussed above in connection with the fat phase, it being appreciated that generally the more hydrophilic additives are best placed in the aqueous phase.

A typical size for an average serving of spread or margarine is 14 grams. Preferred soy protein levels in the margarine or spread are 1 to 25 wt. %, more preferred 2 to 20 wt. %, especially preferred 4 to 20 wt. %, most preferred 4 to 15 wt. %. Preferred isoflavone levels in the margarine or spread are 0.003 to 1.7 wt. %, more preferred 0.07 to 0.71 wt. %, especially preferred 0.11 to 0.36 wt. %, most preferred 0.07 to 0.13 wt. %. Preferred phytosterol levels in the margarine or spread are 0.65 to 21 wt. %, more preferred 3 to 18 wt. %, especially preferred 4 to 12 wt. %, most preferred 5 to 10 wt. %. Preferred calcium levels in the margarine or spread are 0.3 to 7 wt. %, more preferred 0.33 to 3.5 wt. %, especially preferred 0.35 to 1.75 wt. %, most preferred 0.35 to 0.7 wt. %.

Although melatonin may be added, compositions in which melatonin is essentially not present, especially compositions in which melatonin is completely absent, are preferred.

The balance of the spread is largely water, which may be incorporated at levels of up to 99.9% by weight, more generally from 10 to 98%, preferably from 20 to 97% by weight. Spreads according to the invention may be fat- or water-continuous, preferably fat-continuous.

Frozen Confectionery Products

For the purpose of the invention the term frozen confectionery product includes milk containing frozen confections such as ice-cream, frozen yoghurt, sherbet, sorbet, ice milk and frozen custard, water-ices, granitas and frozen fruit purees.

Preferably the level of solids in the frozen confection (e.g. sugar, fat, flavouring etc) is more than 3 wt. %, more preferred from 10 to 70 wt, for example 40 to 70 wt. %.

Ice-cream will typically comprise 2 to 20 wt. % of fat, 0 to 20 wt. % of sweeteners, 2 to 20 wt. % of non-fat milk components and optional components such as emulsifiers, stabilizers, preservatives, flavoring ingredients, vitamins, minerals, etc, the balance being water. Typically ice-cream will be aerated e.g. to an overrun of 20 to 400%, more generally 40 to 200% and frozen to a temperature of from −2 to −200 C, more generally −10 to −30 C. Ice-cream normally comprises calcium at a level of about 0.1 wt. %.

A typical size of an average serving of frozen confectionery material is 66 grams. Preferred soy protein levels in the frozen confectionery are 0.7 to 25 wt. %, more preferred 0.7 to 15 wt. %, especially preferred 1.6 to 12.0 wt. %, most preferred 3 to 9 wt. %. Preferred isoflavone levels in the frozen confectionery are 0.0015 to 0.3 wt. %, more preferred 0.03 to 0.20 wt. %, especially preferred 0.02 to 0.17 wt. %, most preferred 0.008 to 0.09 wt. %. Preferred phytosterol levels in the frozen confectionery are 0.3 to 7.0 wt. %, more preferred 0.3 to 6.0 wt. %, especially preferred 0.6 to 5.0 wt. %, most preferred 0.6 to 3.0 wt. %. Preferred calcium levels are 0.15 to 3 wt. %, more preferred 0.17 to 1.5 wt. %, especially preferred 0.18 to 0.75 wt. %, most preferred 0.18 to 0.3 wt. %.

Tea Based Products

For the purpose of this invention the term tea based products refers to products containing tea or tea replacing herbal compositions e.g. tea-bags, leaf tea, herbal tea bags, herbal infusions, powdered tea, powdered herbal tea, ice-tea, ice herbal tea, carbonated ice tea, carbonated herbal infusions etc.

Typically some tea based products of the invention may need a preparation step shortly before consuming, e.g. the making of tea brew from tea-bags, leaf tea, herbal tea bags or herbal infusions or the solubilization of powdered tea or powdered herbal tea. For these products it is preferred to adjust the level of isoflavones, soy protein, phytosterol and optionally calcium in the product such that one serving of the final product to be consumed has the desired levels of isoflavones, soy protein and phytosterol as described above.

For ice-tea, ice herbal tea, carbonated ice tea, carbonated herbal infusions the typical size of one serving will be 250 ml or 250 grams. Preferred levels of soy protein in these ready-to-drink products are 0.4 to 10 wt. %, more preferred, 1.2 to 8 wt. %, especially preferred 2 to 6 wt. %, most preferred, 2 to 4 wt. %. Preferred levels of isoflavone in these ready-to-drink products are 0.0004 to 0.1 wt. %, more preferred, 0.0008 to 0.05 wt. %, especially preferred 0.0016 to 0.016 wt. %, most preferred, 0.002 to 0.02 wt. %. Preferred levels of phytosterols in these ready-to-drink products are 0.08 to 1.5 wt. %, more preferred, 0.16 to 1 wt. %, especially preferred 0.2 to 0.8 wt. %, most preferred, 0.24 to 0.7 wt. %. Preferred levels of calcium in these ready to drink products are 0.04 to 0.8 wt. %, more preferred, 0.045 to 0.4 wt. %, especially preferred 0.05 to 0.2 wt. %, most preferred, 0.05 to 0.08 wt. %.

For products which are extracted to obtain the final product, generally the aim is to ensure that one serving of 250 ml or 250 grams comprises the desired amounts as indicated above. In this context it should be appreciated than normally only part of the isoflavones present in the tea based product to be extracted will eventually be extracted into the final tea drink. To compensate for this effect generally it is desirable to incorporate into the products to be extracted about 2 times the amount of isoflavones as is desired to have in the extract.

Salad Dressings or Mayonnaise

Generally dressings or mayonnaise are oil in water emulsions. The oil phase of the emulsion generally is 0 to 80 wt. % of the product. For non fat reduced products the level of fat is typically from 60 to 80%, for salad dressings the level of fat is generally 10–60 wt. %, more preferred 15–40 wt. % Low or no fat dressings may for example contain triglyceride levels of 0, 5, 10, 15% by weight.

Dressings and mayonnaise are generally low pH products having a preferred pH of from 2–6.

Dressings or mayonnaise optionally may contain other ingredients such as emulsifiers (for example egg-yolk), stabilizers, acidifiers, biopolymers, bulking agents, flavors, coloring agents etc. The balance of the composition is water which could advantageously be present at a level of 0.1 to 99.9 wt. %, more general 20–99 wt. %, most preferred 50 to 98 wt. %.

A typical size for an average serving of dressings is 30 and mayonnaise is 14 grams. Preferred soy protein levels in the dressings or mayonnaise are 1 to 25 wt. %, more preferred 2 to 20 wt. %, especially preferred 4 to 20 wt. %, most preferred 4 to 15 wt. %. Preferred isoflavone levels in the dressing or mayonnaise are 0.003 to 1.0 wt. %, more preferred 0.07 to 0.67 wt. %, especially preferred 0.10 to 0.33 wt. %, most preferred 0.05 to 0.017 wt. %. Preferred phytosterol levels in the dressings or mayonnaise are 1 to 20 wt. %, more preferred 3 to 17 wt. %, especially preferred 4 to 11 wt. %, most preferred 2 to 6.0 wt. %. Preferred calcium levels in the margarine or spread are 0.3 to 7 wt. %, more preferred 0.33 to 3.5 wt. %, especially preferred 0.35 to 1.75 wt. %, most preferred 0.35 to 0.7 wt. %.

EXAMPLE 1

Materials and Methods

Animals: Male golden Syrian hamsters (SASCO), aged 4 weeks with a body weight of approximately 75 g were obtained from Charles River Laboratories, Inc., Wilmington, Mass., USA. After one-week acclimatization, 120 qualified hamsters (healthy and with similar body weight) were allocated into 6 groups (20 animals per group) based on their body weights. The hamsters were individually housed in Macrolon II cages with a layer of sawdust as bedding. The environment temperature was controlled and a 12 h light-dark cycle (lights on 7:00–19:00 h) was kept. Throughout the study, the animals had free access to food and drinking water. Experimental protocols and procedures were approved by DEC (the Animal Care Committee) of Unilever, the Netherlands.

Chemicals: The fed phytosterols were a mixture of plant sterol-esters provided by Unilever Research, Vlaardingen, NL. Soy protein was a Supro texturized protein supplied by PTI Technologies, St. Louis, Mo., USA. Soy isoflavones (Novasoy 40) were provided by Archer Daniels Midland Company, Decatur, Ill., USA.

Diets: During the acclimatization period, hamsters were fed a basal diet which contained the following components expressed in g/kg dry weight: Casein 161, wheat starch 597, fat 126, mineral mix 40.7, vitamin mix 11.6, choline chloride 2.9. Arbocel (BC-200) 58.1. Fat contributed 30% of the total dietary energy. The fatty acid compositions of the diets were 16.8% saturated fatty acids, 8.4% MUFA and 4.6% PUFA of total dietary energy, which were resembled to those in a typical Western diet. The compositions of the mineral mix and the vitamin mix have been described in detail previously (Reeves P G, Nielsen F H, Fahey G C J. AIN-93 purified diets for laboratory rodents: final report of the American Institute of Nutrition ad hoc writing committee on the reformulation of the AIN-76A rodent diet. J Nutr 1993;123:1939–1951).(13).

During the experimental period, hamsters were fed with six different experimental diets (diet A–F) for five weeks.

Control diet (diet A) contained 20% (w/w) casein and other five experimental diets containing (diet B) 20% casein +0.24% phytosterols, (diet C) 20% soy protein (replacing casein), (diet D) 20% casein+0.022% isoflavones, (diet E) 0.24% phytosterols+20% soy protein (replacing casein), or (diet F) 20% casein+0.24% phytosterols+0.022% isoflavones, respectively. The detailed compositions of the experimental diets are shown in Table 1. Food consumption and body weights were monitored every two weeks.

TABLE 1

The compositions of the experimental diets

| Ingredient | Diet A | B | C | D | E | F |
|---|---|---|---|---|---|---|
| | g/kg diet | | | | | |
| Calcium caseinate | 206.3 | 206.3 | 0 | 206.3 | 0 | 206.3 |
| Soy protein, supro* | 0 | 0 | 206.3 | 0 | 206.3 | 0 |
| Vitamin mix | 11.4 | 11.4 | 11.4 | 11.4 | 11.4 | 11.4 |
| Mineral mix | 39.9 | 39.9 | 39.9 | 39.9 | 39.9 | 39.9 |
| Arbocel (fiber source) | 57 | 57 | 57 | 57 | 57 | 57 |
| Fat | 126.2 | 126.2 | 126.2 | 126.2 | 126.2 | 126.2 |
| Phytosterol | 0 | 2.4 | 0 | 0 | 2.4 | 2.4 |
| Novasoy 40** (isoflavones) | 0 | 0 | 0 | 0.62 | 0 | 0.62 |
| L-cystein hydrochloride | 2.1 | 2.1 | 2.1 | 2.1 | 2.1 | 2.1 |
| Cholin bitartrate | 2.8 | 2.8 | 2.8 | 2.8 | 2.8 | 2.8 |
| Cholesterol | 0.8 | 0.8 | 0.8 | 0.8 | 0.8 | 0.8 |
| Maiz starch | 554.3 | 554.3 | 554.3 | 554.3 | 554.3 | 554.3 |
| Total | 1000.8 | 1003.2 | 1000.8 | 1001.5 | 1003.2 | 1003.9 |

*Supro contains 0.981 (mg/g, w/w) isoflavones. 206 g Supro provided 202 mg isoflavones to each kilogram diet.
**Novasoy-40 contains 352 (mg/g, w/w) isoflavones. 0.62 g Novasoy provided 218 mg isoflavones to each kilogram of diet.

Sample collection and chemical analysis: Triplicates were collected from each badge of the experimental diets in order to evaluate the dietary composition and the homogeneity of the tested components. Dietary isoflavones were determined by using a GC method.

Blood samples: At termination of the study, hamsters were deprived of food overnight (approximately 16 hours) and then exsanguinated under anesthesia using a gaseous mixture of $N_2O$, $O_2$ together with halothane. Orbital blood samples were collected in EDTA tubes/4 ml. Plasma total cholesterol (TC) and triacylglycerol (TG) concentrations were determined by enzymatic assays on the COBAS analyser.

Statistical analysis: Data are presented as the mean±SEM. Statistical differences were assessed by means of ANOVA. Student-Newman-Keuls test was used to assess the differences between the groups of treatments. This statistical analysis was conducted by using software SAS (version 6.12). Significant difference was based on a p-value<0.05.

Results

Isoflavone Contents in the Diets

The actual contents of isoflavones in experimental diets were determined and the results are shown in Table 2, where isoflavones are presented in the form of aglycones. Diet A (control) and B contained negligible amount of isoflavones. Isoflavone-diets (diet D and F) contained 155–158 (mg/kg diet) isoflavones, which was 76–78% of the total amount of isoflavones contained in soy-protein diets (203–213 mg/kg diet). Mainly less genistein was contained in isoflavone-diets than in soy protein diets. Due to unknown reasons, the chemically analytical values of dietary isoflavone concentrations (155–158 mg/kg) are lower than the calculated values (218 mg/kg) in diet D and F, which were based on chemically analytical values of the Supro and Novasoy (see table 1).

TABLE 2

The concentrations of isoflavones in experimental diets

| Group | Diets | Daidzein | Glycitein | Genistein | Total |
|---|---|---|---|---|---|
| A | Control | Nd | Nd | Nd | nd |
| B | Phytosterols | Nd | Nd | Nd | nd |
| C | Soy proteins | 63.2 ± 2.6 | 56.4 ± 4.6 | 83.9 ± 4.0 | 203 ± 11.2 |
| D | Isoflavones | 60.0 ± 0.9 | 89.5 ± 2.1 | 6.0 ± 0.3 | 155.5 ± 3.4 |
| E | Phytosterols + Soy proteins | 66.4 ± 0.9 | 59.2 ± 2.4 | 88.1 ± 0.2 | 213.7 ± 3.1 |
| F | Phytosterols + isoflavones | 61.0 ± 1.0 | 91.5 ± 1.2 | 5.8 ± 0.3 | 158 ± 1.9 |

Isoflavones are calculated as form of aglycones. Data are presented as mean ± SD obtained from two batches of diets, each batch was analysed as duplicates.
"nd" means "not detectable."

Food Intake and Animal Growth

There were no significant differences in food intake between any experimental groups. During the 5 weeks of the experimental feeding, the hamsters had gained body weight in a similar way, which seemed not to be affected by any treatment compared with control.

Plasma Lipid Concentrations

The effects of experimental diets on fasting plasma concentrations of TC and TG are shown in table 3. Compared to the control diet, phytosterol-diet and soy-protein-diet reduced plasma TC by 13% and 8.6%, respectively, while isoflavone-containing had no effect. The combination of phytosterols and soy protein in the diet resulted in 25.7% decrease of plasma TC, indicating not less than an additive or a synergistic cholesterol-lowering effect. The plasma TG concentrations were not influenced by the diets containing phytosterols, soy protein or isoflavones alone, while the combination of phytosterols and soy protein in the diet significantly reduced plasma TG by 37%.

TABLE 3

Plasma TC and TG concentration (mmol/L)

| Group | Diets | TC | TG |
|---|---|---|---|
| A | Control | $6.76 \pm 0.20^A$ | $6.75 \pm 0.73^A$ |
| B | Phytosterols | $5.88 \pm 0.15^C$ | $5.69 \pm 0.50^{AB}$ |
| C | Soy proteins | $6.20 \pm 0.16^{CB}$ | $5.98 \pm 0.53^{AB}$ |
| D | Isoflavones | $6.58 \pm 0.18^{AB}$ | $6.32 \pm 0.55^A$ |
| E | Phytosterols + Soy proteins | $5.02 \pm 0.14^D$ | $4.26 \pm 0.32^B$ |
| F | Phytosterols + isoflavones | $6.07 \pm 0.14^{CB}$ | $6.57 \pm 0.48^A$ |

Hamsters (n = 20 per group) were fed indicated diets for 5 weeks. Blood samples were collected at a fasting state. Plasma lipid concentrations were determined as described in the Section of Materials and Methods. Results are presented as mean ± SEM. The mean values which do not share a common superscript letter are significantly different ($P < 0.001$).

Discussion

This study provides further evidence that both phytosterol- and soy-protein diets have hypocholesterolemic effects compared with casein-control diet in hamsters. The novel finding of this study is that the combination of intervention of phytosterols and soy protein give a clear additive hypocholesterolemic effect. A previous hamster study conducted in a similar experimental conditions demonstrated that by increasing a dietary phytosterols supplementation from 0.24 to 0.48% (w/w) no extra hypocholesterolemic effect was achieved (Trautwein et al 1999, unpublished observations). The additive cholesterol lowering effect of the combination of phytosterols and soy protein is therefore unexpected and would provide a useful tool in anti-hypercholesterolemia.

Isoflavones as part of soy protein have been postulated to account for the hypocholesterolemic effect of soy protein (19;20). However, the present data do not support the idea as plasma TC and TG were not influenced by isoflavone-containing diets when compared with the control diet. Our data suggests that isoflavones, at least daidzein and glycitein alone, might not account for the hypocholesterolemic effect of soy protein as the contents of daidzein and glycitein in isoflavone-containing diets were comparable to those in soy protein-containing diets. The results are in agreement with those of a human study in which blood lipid profiles were not improved in postmenopausal women consuming soy isoflavone tablets (equivalent to 80 mg/d aglycone)(21). Crouse et al (22) demonstrated in a human study that soy protein alone (alcohol-extracted soy protein) had no cholesterol-lowering effect, whereas isoflavone containing soy protein (1.5 mg isoflavone aglycone/g protein) remarkably lowered (−8%) LDL cholesterol in hyperlipidemea individuals. Hodgson et al recently reported that intake of 55 mg isoflavonoids (predominantly in the form of genistein) per day did not improve plasma lipid profile in healthy human subjects (24).

EXAMPLE IV

Frozen Confectionery Product

The following ice-cream products are prepared by freezing in conventional ice-cream freezers.

Product A

| Description | wt % |
|---|---|
| MILKFAT | 4.0% |
| NONFAT MILK | 14.0% |
| LIQUID SUCROSE (DRY WT) | 13.5% |
| LIQUID CORN 36 DE 80% | 7.75% |
| ENRICH 301 | 1.3% |
| STAR VITE A(25) 8.2#/ga | 0.0027% |
| 10/12 AMBER COCOA POWDER LB | 2.3% |
| Supro ® (soy protein isolate) | 12.0 |
| SoyLife ® (soy germ flour) | 0.50% |
| Novasoy ® 40 (isoflavones) | 0.1 |
| LIQUID SUGARED EGG YOLKS | 2.87% |
| WATER | balance |

Product B

| Description | wt % |
|---|---|
| MILKFAT PACKAGED | 4.% |
| NONFAT MILK PACKAGED | 14.0% |
| LIQUID SUCROSE (DRY WT) | 14.0 |
| LIQUID CORN 36 DE 80% | 3.87% |
| ENRICH 301 | 1.3% |
| STAR VITE A(25) 8.2#/ga | 0.0034% |
| Supro (soy protein isolate) | 9 |
| Sterol Esters | 5 |
| Novasoy ® 40 (isoflavones) | 0.1 |
| SoyLife ® (soy germ flour) | 0.55% |
| WATER | Balance |

EXAMPLE V

Tea Based Products

Iced Tea Mix I

| Ingredient | Wt parts |
|---|---|
| MALTODEXTRIN | 29.25 |
| TEA POWDER | 8.7 |
| ASPARTAME | |
| LEMON OIL POWDER | 0.95 |
| LEMON ESSENCE POWDER | 0.54 |
| MALIC ACID | 12.3 |
| OIL COATED MALIC ACID | 4.78 |
| MAGNESIUM OXIDE | 0.18 |
| Novosoy ® 40 (Isoflavones) | 1.0 |
| VITAMIN PREMIX, = XR05837000 | 0.30 |
| Supro ® (soy protein isolate) | 20.0 |
| Sterol ester | 22.0 |

3.3 grams of the product can advantageously be used to prepare a serving of iced tea of 250 mls.

Iced Tea Mix II

| Ingredient | Wt parts |
|---|---|
| MALTODEXTRIN | 29.93 |
| TEA POWDER | 8.7 |
| ASPARTAME | |
| PEACH FLAVOR | 3.6 |
| N&A APRICOT FLAVOR | 1.17 |
| CITRIC ACID | 9.05 |
| OIL COATED CITRIC ACID | 1.27 |
| MAGNESIUM OXIDE | 0.18 |
| STEROL ESTER | 22 |

-continued

| Ingredient | Wt parts |
| --- | --- |
| VITAMIN PREMIX, = XR05837000 | 0.31 |
| NOVOSOY ® 40 (Isoflavones) | 1.0 |
| SUPRO ® (Soy Protein Isolate) | 20.0 |

This mix can be used in the same way as mix I.

EXAMPLE VI

Caesar Dressing

A dressing according to the following formulation is prepared.

| Ingredient | Wt Parts |
| --- | --- |
| DISTILLED WHITE VINEGAR | 2.0 |
| CANOLA OIL | 15.3 |
| SUCROSE | 7.5 |
| GRATED ROMANO CHEESE | 3.25 |
| SODIUM CHLORIDE GRANULAR | 2.2 |
| GARLIC POWDER | 3.0 |
| ANCHOVY PASTE | 1.5 |
| BLACK PEPPER | 0.5 |
| XANTHAN GUM | 0.27 |
| PROPYLENE GLYCOL ALGINATE | 0.10 |
| BALSAMIC VINEGAR | 3.07 |
| SOYLIFE ®** (soy germ flour) | 1.10 |
| VITAMIN PREMIX, ROCHE XR05837000 | 0.033 |
| GLUCONAL CALCIUM* | 3.35 |
| SODIUM BENZOATE GRANULAR | 0.09 |
| SORBIC ACID | 0.12 |
| EDTA | 0.007 |
| PHOSPHORIC ACID, 75% CONC. | 1.0 |
| POLYSORBATE 60 | 0.10 |
| SUPRO ® (Soy protein isolate) | 8.5 |
| STEROL ESTERS | 6.0 |
| CARAMEL POWDER | 0.04 |
| Water | To 100 |

*Calcium gluconate 80%/Calcium Lactate 20%
**Particle size 80% through 60 U.S. sieve size.

Italian Dressing

An Italian dressing according to the following formulation is prepared:

| Ingredient | Parts By Weight |
| --- | --- |
| HIGH FRUCTOSE CORN SYRUP | 13.2 |
| CANOLA OIL | 15.3 |
| RED WINE VINEGAR | 1.4 |
| SODIUM CHLORIDE GRANULAR | 1.9 |
| PHOSPHORIC ACID, 75% CONC. | 1.0 |
| XANTHAN GUM | 0.25 |
| MINCED GARLIC | 0.91 |
| BLK PEPPER MED | 0.18 |
| RICE WINE VINEGAR, 10% | 6.85 |
| SODIUM BENZOATE GRANULAR | 0.085 |
| SORBIC ACID | 0.061 |
| SoyLife ®** (soy germ flour) | 1.1 |
| VITAMIN PREMIX ROCHE XR05837000 | 0.033 |
| GLUCONAL CAL* | 3.35 |
| EDTA | 0.0066 |
| HERB DE PROVENCE | 0.19 |
| MINCED ONION | 0.19 |
| SUGAR | 2.25 |
| SUPRO ® (Soy protein isolate) | 8.5 |
| STEROL ESTERS | 6.0 |
| ANNATTO COLOR | 0.0047 |
| WATER | To 100 |

*Calcium gluconate 80%/Calcium Lactate 20%
**Particle size 80% through 60 U.S. sieve size

EXAMPLE VII

Four variations of ice cream flavors are prepared first by preparing a white mix and a chocolate mix as follows:

I. White Mix

| Ingredient | % weight |
| --- | --- |
| Milk fat | 4.50 |
| Non-fat milk solids | 15.25 |
| Liquid sugar | 14.00 |
| Liquid corn syrup | 3.88 |
| Stabilizer - guar/locust bean gum | 0.15 |
| Star vitamin A palmitate | 0.0034 |
| Roche vitamin mix: | 0.015 |
| Alpha-Tocopheryl acetate (vitamin E) | |
| Cyanocobalamin (vitamin B$_{12}$) | |
| Pyridoxine Hydrochloride (vitamin B$_6$) | |
| NOVOSOY ® 40 (Isoflavones) | 0.1 |
| STEROL ESTERS | 5 |
| SUPRO ® (Soy protein isolate) | 9 |
| SoyLife ® (soy germ flour) | 0.56 |
| Water to 100% | 47.55 |

II. Chocolate Mix

| Ingredient | % weight |
| --- | --- |
| Milk fat | 4.00 |
| Non-fat milk solids | 15.25 |
| Liquid sugar | 13.47 |
| Liquid corn syrup | 7.75 |
| Stabilizer - guar/locust bean gum blend | 0.15 |
| Cocoa powder | 2.30 |
| SoyLife ® (soy germ flour) | 0.505 |
| Liquid sugared egg yolks | 2.87 |
| Star vitamin A palmitate | 0.0027 |
| Roche vitamin mix: | 0.0151 |
| Alpha-Tocopheryl acetate (vitamin E) | |
| Cyanocobalamin (vitamin B$_{12}$) | |
| NOVOSOY ® ® 40 (Isoflavones) | 0.1 |
| SUPRO (Soy protein isolate) | 9.0 |
| STEROL ESTERS | 5.0 |
| Pyridoxine Hydrochloride (vitamin B$_6$) | |
| Water to 100% | 39.6 |

The Ice Cream Flavors then use the white or chocolate mix to prepare different flavors as follows:

| | Ingredients | % weight |
| --- | --- | --- |
| A. French chocolate ice cream | Chocolate mix | 92.78 |
| | Milk chocolate flakes | 7.17 |
| | Vanilla flavor | 0.05 |
| B. Vanilla ice cream | White mix | 99.60 |
| | Vanilla flavor | 0.40 |
| C. Vanilla fudge ice cream | White mix | 90.74 |
| | Vanilla flavor | 0.364 |
| | Fat free liquid fudge variegate | 8.90 |
| D. Caramel praline ice cream | White mix | 82.35 |
| | Vanilla flavor | 0.40 |
| | Liquid caramel variegate | 11.65 |
| | Praline nuts & toffee (particulate) | 5.60 |

EXAMPLE VIIIa

Spread

| Ingredients | % |
|---|---|
| Oil Phase | 40.00 |
| Canola Oil | 19.08 |
| Bean Oil | 1.77 |
| Partially hydrogenated bean oil, melting point 42° C. | 5.70 |
| Lecithin | 0.22 |
| Saturated distilled monoglyceride (iodine value <5) | 0.22 |
| Flavor | Trace |
| STEROL ESTER | 13.01 |
| Vitamin A | 0.01 |
| Aqueous phase | 60.00 |
| Water | 35.13 |
| Salt | 1.50 |
| Lactic Acid | 0.09 |
| Potassium Sorbate | 0.11 |
| Calcium disodium EDTA | 0.01 |
| Pork Gelatin | 2.00 |
| NOVOSOY ® 40 | 0.5 |
| SUPRO ® (Soy protein isolate) | 15 |
| Beta tricalcium phosphate | 1.88 |
| Xanthan gum | 0.10 |
| Artificial color Yellow 5 | 0.04 |
| Titanium dioxide | 0.28 |
| Vitamin mix B6, B12 & E | 0.07 |
| Total | 100.00 |

EXAMPLE VIIIb

Spread—Low Calcium

| Ingredients | Parts by weight |
|---|---|
| Oil Phase | 40.00 |
| Canola Oil | 19.08 |
| Bean Oil | 1.77 |
| Partially hydrogenated bean oil, melting point 42° C. | 5.70 |
| Lecithin | 0.22 |
| Saturated distilled monoglyceride (iodine value <5) | 0.22 |
| Flavor | Trace |
| STEROL ESTER | 13.01 |
| Vitamin A | 0.01 |
| Aqueous phase | 60.00 |
| Water | 35.13 |
| Salt | 1.50 |
| Lactic Acid | 0.09 |
| Potassium Sorbate | 0.11 |
| Calcium disodium EDTA | 0.01 |
| Pork Gelatin | 2.00 |
| NOVOSOY ® 40 | 0.5 |
| SUPRO ® (Soy protein isolate) | 15 |
| Xanthan gum | 0.10 |
| Artificial color Yellow 5 | 0.04 |
| Titanium dioxide | 0.28 |
| Vitamin mix B6, B12 & E | 0.07 |

The Spreads of Examples VIIIa and VIIIb are Prepared by the Following Procedure, except that Tricalcium Phosphate Addition is Omitted in Example VIIIb The oil phase is prepared by heating the liquid oil and partially hydrogenated bean oil in a tank to 65° C. The emulsifiers, lecithin and monoglycerides are mixed and the mixture is held for 30 minutes to completely melt the fat crystals.

Vitamin A, flavor are added to the heated oil phase.

The aqueous phase is prepared by adding xanthan gum to the water at 40° C. in a tank. After hydrating the gum for 15 minutes, tricalcium phosphate is dispersed. All the other dry ingredients are added and mixed with a high shear mixer to obtain a homogeneous aqueous phase. The contents in the tank are batch pasteurized by heating to 80° C. and holding for 5 minutes and cooled to 55° C.

The fat and aqueous phases are mixed together at approximately 55° C. in a heated tank in a ratio of approximately 40 parts fat phase to 60 parts aqueous phase. This emulsion is water continuous. The emulsion is then passed through a cooled, scraped-surface heat exchanger (A-unit) where the emulsion is cooled to a temperature where the fat will begin to crystallize (few degrees C below the alpha point 4° C.) and the aqueous phase will begin to gel, if the aqueous phase has the gelling agents, and/or there is increase in viscosity if only thickening agents are present in the aqueous phase. The cooled emulsion is then passed into a slowly agitated, variable speed crystallizer (C*-unit) where the product is inverted from a water-continuous emulsion to a fat-continuous emulsion by quickly increasing the shaft speed. The inversion is aided by injecting 100% fat into the system. The C* unit is referred to as the inverter unit. The inverter speed is 1000 rpm. The shaft speed in the inverter unit depends on its dimensions but normally varies from 200–2000 rpm. The fat continuous emulsion is passed into an additional C unit running at shaft speed of 300 rpm to provide gentle mixing while the fat continues to crystallize from the alpha to beta prime form.

Extra cooling capacity can be added to the process by including additional A-units. Extra residence time can be added to the process by including additional C-units.

As indicated above, a source of isoflavones is soy germ flour, SoyLife® as marketed by SoyLife Nederland B.V. and has subsidiaries in the US in Minneapolis, Minn., USA.

The composition of SoyLife® is approximately as follows:

| Ingredient | wt. % |
|---|---|
| Isoflavones[1] | 3% |
| Saponins | 4% |
| Protein | 40% |
| Fat | 11% |
| Fiber | 4% |
| Ash | 5% |
| Carbohydrates | 35% |
| Cholesterol | 0% |
| Tocopherols | 0.05% |
| α-Tocopherol | 0.008% |
| Lecithin | 2% |
| Water | balance |

[1]glucosides

Novosoy® brand soy products may be obtained from Archer Daniels Midland (ADM) of Decatur Ill. Supro® brand protein isolates may be obtained from Protein Technologies Inc. of St. Louis, Mo. Methods of making sterol esters are disclosed in, for example, U.S. Pat. Nos. 6,231,915, 6,106,886, 6,231,915, 6,184,397, 6,106,886, 6,031,118, 5,958,913, 5,958,913, or 5,892,068.

The following vitamin mixes are used above:

XR05837000 (ex Roche):

| Ingredient | wt. % |
|---|---|
| Vitamin B6 | 2.9% |
| Vitamin $B_{12}$ | 7.8% |
| Vitamin E | 72% |
| Maltodextrin | balance |

GLATT PH990097:

| Ingredient | wt. % |
|---|---|
| Calciumlactate | 73.8 |
| Vitamin B6 | 0.29% |
| Vitamin B12 | 0.78% |
| Vitamin E | 7.2% |
| Maltodextrin | balance |

Unless stated otherwise or required by context, the terms "fat" and "oil" are used interchangeably herein. Where a phase is said to constitute essentially the entire product, it is meant that such phase constitutes at least 98 wt. %, especially more than 99 wt. % of such product. Unless otherwise stated or required by context, percentages are by weight.

What is claimed is:

1. A process of lowering blood cholesterol in an animal comprising feeding the animal a composition comprising an effective amount of at least one vegetable protein, at least one phytosterol and at least one isoflavone and at least 7 wt % polyunsaturated fatty acid moieties, wherein the vegetable protein, phytosterol and isoflavone synergistically lower the blood cholesterol.

2. An ingestable composition comprising a cholesterol lowering effective synergistic amount of vegetable protein, phytosterol and isoflavone and at least 7 wt % polyunsaturated fatty acid moieties.

3. The process according to claim 1 wherein said isoflavone is selected from the group consisting of genistein, daidzein and glycitein.

4. The process according to claim 1 wherein said phytosterol is selected from the group consisting of Beta sitosterol Beta sitostanol, campesterol and stigmasterol.

5. The process according to claim 1 wherein said composition includes less than 4 wt. % dietary fiber.

6. The process according to claim 1 wherein said composition includes less than 3 wt. % dietary fiber.

7. The process according to claim 5 wherein said composition includes no dietary fiber.

8. The composition according to claim 2 wherein said composition includes less than 4 wt. % dietary fiber.

9. The composition according to claim 2 wherein said composition includes less than 3 wt. % dietary fiber.

10. The composition according to claim 2 wherein said composition includes no dietary fiber.

11. The process according to claim 1 wherein said vegetable protein includes soy protein.

12. The composition according to claim 2 wherein said vegetable protein includes soy protein.

13. The process according to claim 1 wherein the animal is a human.

14. The process according to claim 1 wherein the process comprises feeding the animal more than one serving of one or more foods.

15. The process according to claim 14 wherein said one or more foods includes at least one serving of spreads.

16. The process according to claim 1 wherein the composition further comprises calcium salt at less than 0.5 wt. % calcium salt.

17. The process according to claim 16 wherein the composition comprises less than 0.1 wt. % calcium salt.

18. The process composition according to claim 2 wherein the composition further comprises calcium salt at less than 0.5 wt. % calcium salt.

19. The composition according to claim 18 wherein the composition comprises less than 0.1 wt. % calcium salt.

20. The process according to claim 1 wherein the composition comprises calcium at less than 0.5 wt. % calcium measured as calcium.

21. The process according to claim 20 wherein the composition comprises less than 0.3 wt. % calcium, measured as calcium.

22. The process composition according to claim 17 wherein the composition comprises less than 0.1 wt. % calcium measured as calcium.

23. The process according to claim 2 wherein the composition comprises calcium at less than 0.5 wt. % calcium measured as calcium.

24. The process according to claim 23 wherein the composition comprises less than 0.3 wt. % calcium, measured as calcium.

25. The process composition according to claim 24 wherein the composition comprises less than 0.1 wt. % calcium measured as calcium.

26. The composition according to claim 18 wherein the composition comprises less than 0.1 wt. % calcium salt.

27. A process of lowering blood cholesterol in an animal comprising feeding the animal a composition comprising from 1 to 25 g of at least one vegetable protein, from 0.2 to 3 g of at least one phytosterol from 5 to 150 mg of at least one isoflavone, and at least 7 wt % polyunsaturated fatty acid moieties.

28. An ingestable composition comprising a cholesterol lowering effective synergistic amount from 1 to 25 g of at least one vegetable protein, from 0.2 to 3 g of at least one phytosterol from 5 to 150 mg of at least one isoflavone, and at least 7 wt % polyunsaturated fatty acid moieties.

29. A process of lowering blood cholesterol in an animal comprising feeding the animal per day from 1 to 25 g of at least one vegetable protein, from 0.2 to 3 g of at least one phytosterol from 5 to 150 mg of at least one isoflavone, and at least 7 wt % polyunsaturated fatty acid moieties.

30. The process according to claim 1 wherein said composition includes less than 1 wt % dietary fiber.

31. The process according to claim 1 wherein from the composition comprises 1 to 25 g soy or other vegetable protein, from 5 to 150 mg isoflavone and up to 1.7 g phytosterol.

32. The process according to claim 31 wherein the composition comprises from 0.2 to 1.7 g phytosterol.

* * * * *